United States Patent [19]

Horton et al.

[11] Patent Number: 5,235,860

[45] Date of Patent: Aug. 17, 1993

[54] BAND STRETCH MEASURING SYSTEM

[75] Inventors: Gilbert L. Horton, Kernersville; Herman M. Respess, Tobaccoville; Eddie D. Poole, Lexington; William A. Borst, Burlington; Terri L. McBride, Walkertown, all of N.C.

[73] Assignee: Sara Lee Corp., Winston-Salem, N.C.

[21] Appl. No.: 811,456

[22] Filed: Dec. 19, 1991

[51] Int. Cl.$^5$ .............................................. G01N 3/08
[52] U.S. Cl. ..................................................... 73/832
[58] Field of Search .......................... 73/159, 789–792, 73/826, 831–833, 832

[56] References Cited

U.S. PATENT DOCUMENTS

| | | | |
|---|---|---|---|
| 922,524 | 5/1909 | Schopper | 73/832 |
| 1,817,617 | 8/1931 | Gosch | 73/832 |
| 1,846,241 | 2/1932 | Albertoni | 73/792 |
| 2,187,914 | 1/1940 | Reitan | 73/832 |
| 2,706,402 | 4/1955 | Jones, Sr. | 73/832 |
| 3,039,299 | 6/1962 | Roof. | |
| 3,316,757 | 5/1967 | Fletcher et al. | 73/831 |
| 3,444,728 | 5/1969 | Burns. | |
| 3,639,987 | 2/1972 | Page | 73/832 |
| 5,094,110 | 3/1992 | Porter et al. | 73/832 |

FOREIGN PATENT DOCUMENTS 0007287 1/1978 Japan ..................................... 73/831

Primary Examiner—Robert Raevis

[57] ABSTRACT

A predetermined force is applied to the waistband of a hosiery article to determine the waistband's maximum elongation, for the predetermined force and the band subsequently is relaxed to a preset dimension and the compression force exerted by the band is measured and recorded. The apparatus includes a stationary and a displaceable finger over which the waistband is stretched. A fluid cylinder moves the displaceable finger away from the stationary finger, producing the application of a predetermined force. Once the distance between fingers is measured, the cylinder moves the displaceable finger to position it a predetermined distance from the stationary finger and the compressive force applied by the waistband is measured and recorded. In order to insure that the displaceable finger is stopped with the exact predetermined distance between fingers, a calibration stop is first conducted to determine the distance the displaceable finger moves before it actually stops after receiving a stop signal.

8 Claims, 6 Drawing Sheets

BAND STRETCH MEASURING SYSTEM

BACKGROUND, BRIEF SUMMARY AND OBJECTS OF THE INVENTION

This invention relates generally to the art of testing hosiery articles, and more particularly to the measuring of the elastic characteristics of the welt or waistband of hosiery articles used in the formation of pantyhose garments.

The waistbands are stretched by applying a predetermined large but non-destructive force thereto to determine the waistband's elongation and fit characteristics. The system then measures and records the elastic compressive force exerted by the band when the band is relaxed to a preset dimension. Multiple compressive forces may be performed on the same hosiery article.

In the formation of pantyhose garments, a pair of aligned, clamped hosiery blanks or tubular articles have the band end portions severed a prescribed distance and then stretched a significant amount prior to sewing together to define the panty portion of the garment. U.S. Pat. No. 4,188,898, for example, discloses apparatus for stretching the aligned blanks from the FIG. 12 position to the FIG. 13 position. Thus, the present invention provides a measuring system for testing hosiery articles to determine whether such articles fall within acceptable "fit" parameters and can survive automatic sewing operations as disclosed in U.S. Pat. No. 4,188,898.

One of the primary objects of the invention is the provision of a system for testing the bands of hosiery articles to determine the stretch characteristics thereof and ascertain that the "fit" of a resultant garment will be within an acceptable range.

Another object of the invention is the provision of a system for recording the stretch of a waistband when a predetermined force is applied thereto, and for recording compressive forces applied to the waistband at predetermined stops.

Still another object of the invention is the provision of a system for providing a calibrating stop prior to the waistband retracting to a first stop position where compressive forces are recorded.

A further object of the invention is the provision of a measuring system which is more accurate than prior known devices and which is quick and convenient to operate.

Other objects and advantages of the invention will be understood more fully by reference to the drawing and the accompanying detailed description.

BRIEF DESCRIPTION OF THE DRAWING

FIG. 6 is a fragmentary end elevational view of a band supporting finger and mounting means therefore;

DETAILED DESCRIPTION OF THE INVENTION

Figure 1:
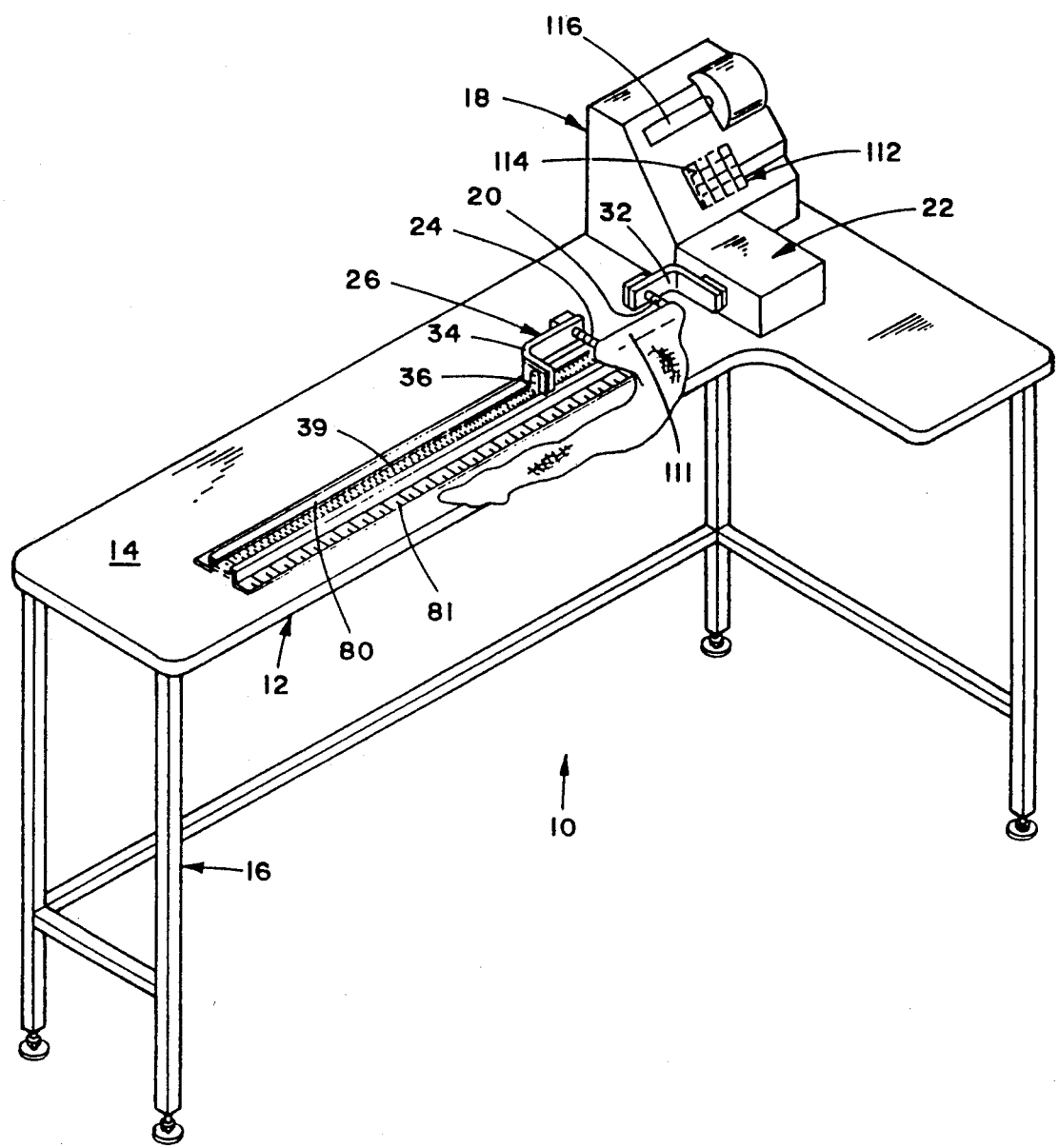
FIG. 1 is a fragmentary perspective view of one embodiment of the testing system of the present invention.
Figure 2:
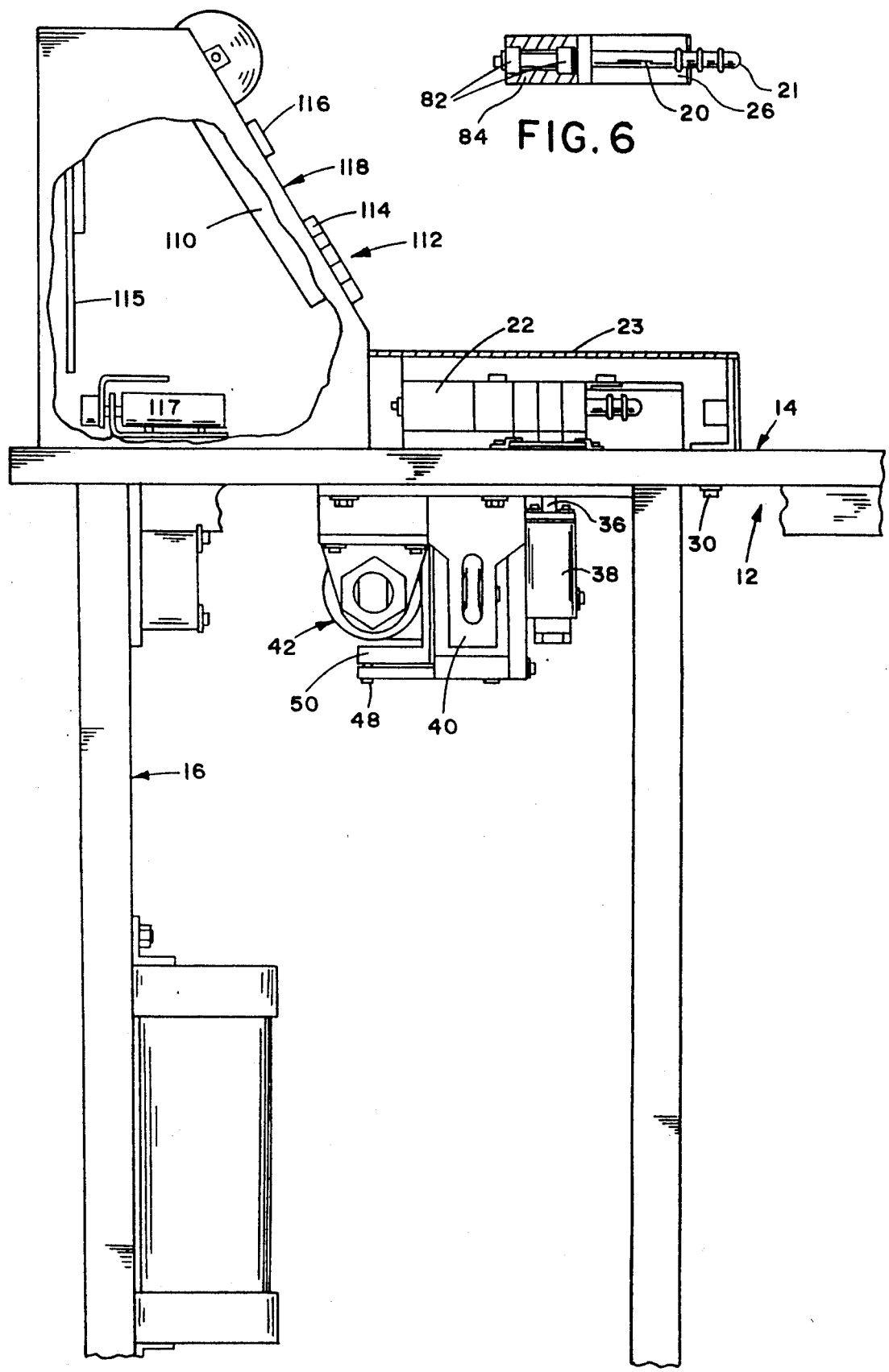
FIG. 2 is an enlarged end elevational view, partially in section, of the system.

Referring to the drawing, and initially to FIG. 1, the measuring apparatus 10 includes a table 12 having a planar surface 14 and a support structure 16, a controller 18, a stationary finger 20 coupled to a load cell 22, a displaceable finger 24, and an assembly 26 for selectively displacing the finger 24 to calibrating and compressive force positions.

The fingers 20 and 24 are positioned above the planar surface 14, and each terminates in an end portion 21 having a series of o-rings extending therearound.

The load cell 22 encompassed in housing 23 is supported on the planar surface 14 by conventional fasteners 30. Secured to the load cell is a generally L-shaped bracket 32 having the finger 20 supported thereon. Force applied by an article waistband to finger 20 is translated into an electrical signal which is directed to the controller 18.

In a preferred embodiment of the invention, the assembly 26 for selectively displacing the finger 24 responsive to signals from the controller includes a bracket 34 having finger 24 supported thereby, a finger shaft 36 which is carried by a bushing 37 on finger plate 38, a Thompson rod assembly including a carriage 40 and rail 43, and a rodless cylinder 42 for displacing the carriage 40. The finger shaft 36 extends through an elongated slot 39 in the planar surface 14.

The end portions of the rodless cylinder 42 and the rail 43 of the Thompson rod are secured to the underneath portion of the planar surface 14 by suitable fasteners 44. The carriage 40 includes a yoke plate 46 which is provided for coupling to a pin 48 fixed to a bracket 50 which, in turn, is coupled to the slide member 52 of the rodless cylinder 42.

Figure 3:
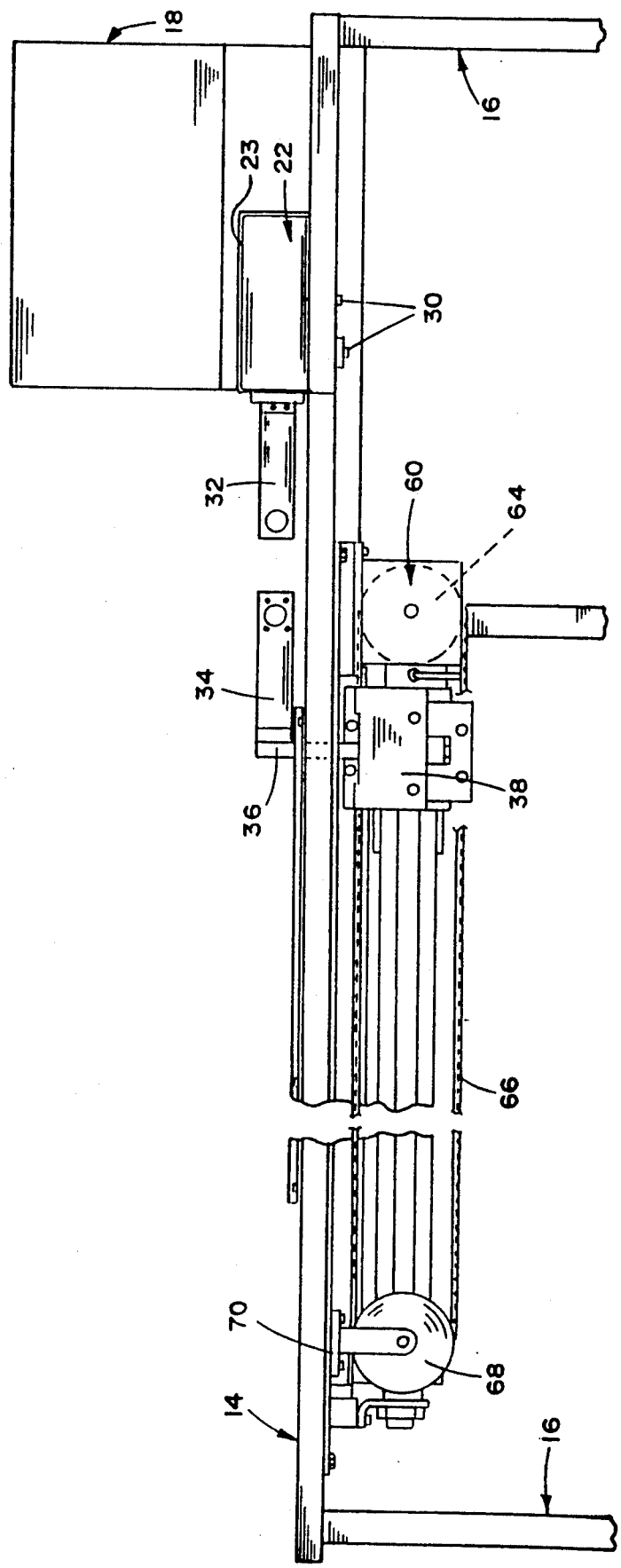
FIG. 3 is an enlarged fragmentary, front elevational view of the system.
Figure 4:
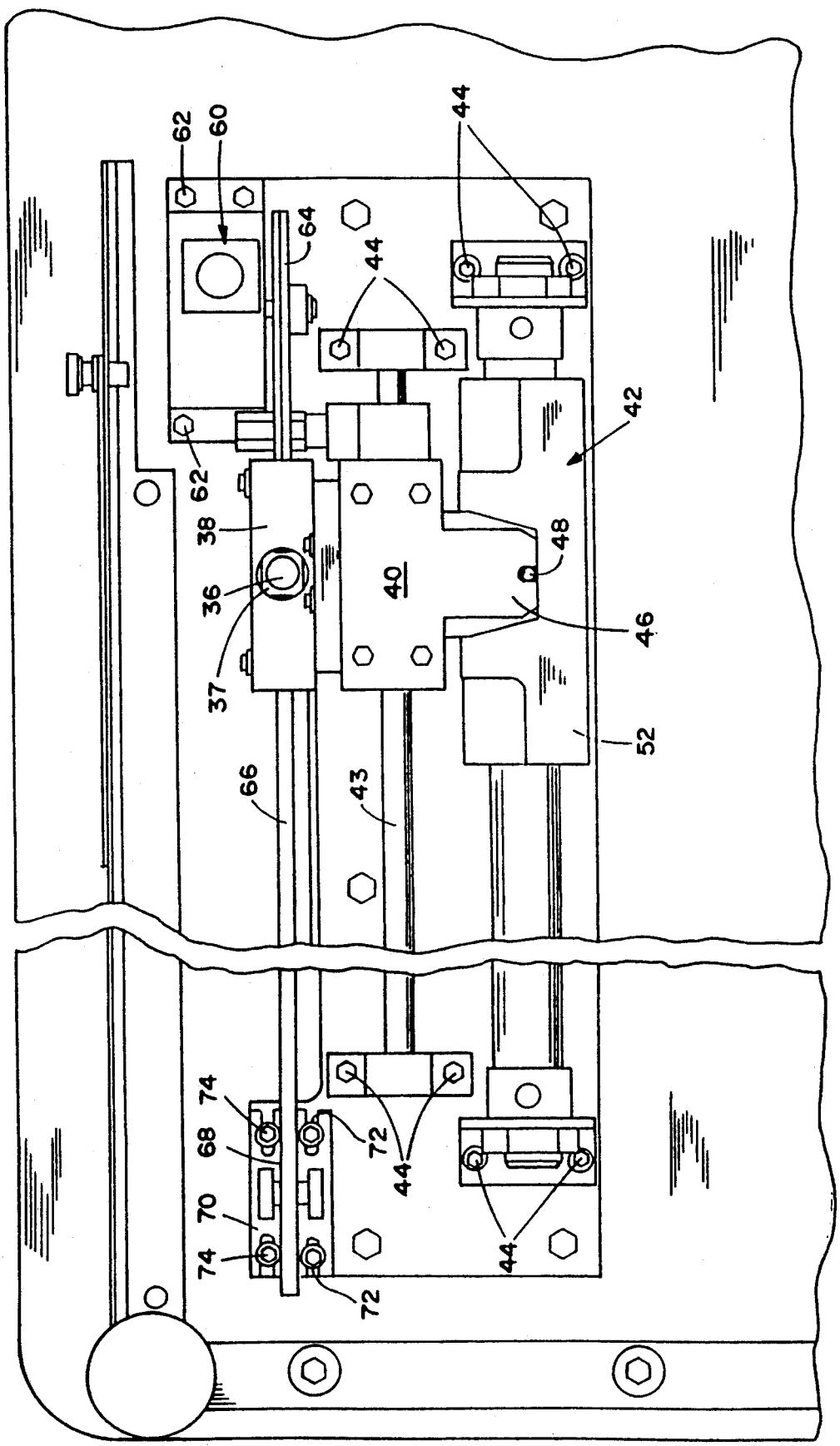
FIG. 4 is a fragmentary, enlarged, bottom plan view of apparatus of FIG. 1.

An encoder 60, FIGS. 3 and 4, is mounted by fasteners 62 to the lower portion of the planar surface 14. The encoder includes a pulley 64 over which is directed a timing belt 66. The belt also passes over an adjustable tensioner pulley 68. The pulley 68 is supported in a belt tensioner stand 70, FIGS. 3 and 4, having slots 72 therein for receiving fasteners 74 for adjustably positioning the pulley 68. The encoder generates a pulse every 0.001 inch of movement of the belt 66 and transmits such pulses to the controller 18.

The timing belt 66 is coupled to the finger plate 38 for movement therewith, and upon displacement of the finger plate by the rodless cylinder 42, the belt drives the encoder and feeds signal pulses to the controller 18.

An elongated nylon filament/seal member 80, is positioned over the slot permitting displacement of the finger shaft 36 therethrough. The member 80 is secured to the planar surface 14 and may be provided with a scale 81 thereon, as shown by FIG. 1.

Referring to FIGS. 3 and 6, the stationary finger 20 coupled to the load cell 22 is rotatably mounted in bearings 82 supported by housing 84 on bracket 32.

Figure 5:
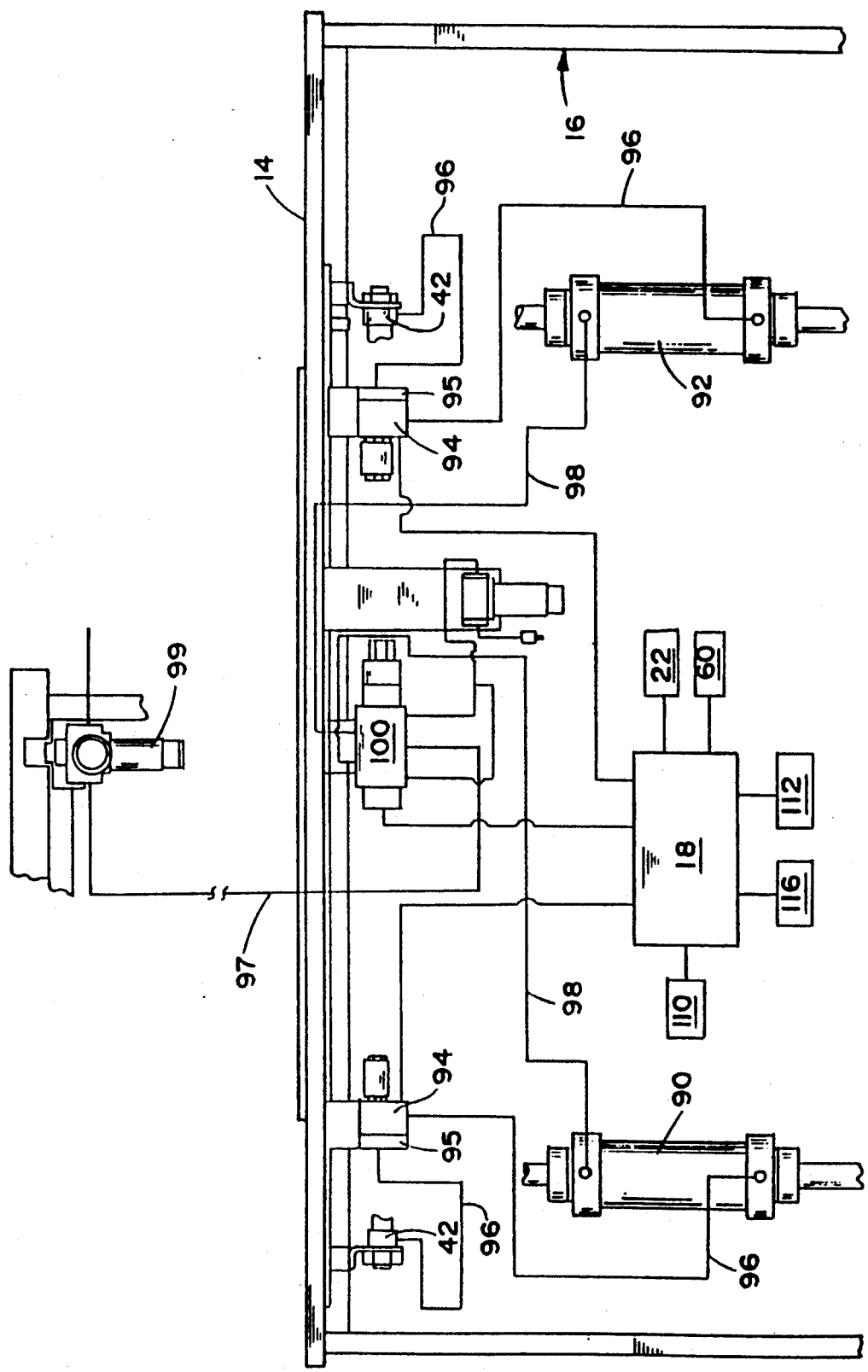
FIG. 5 is a fragmentary, enlarged, front elevational view of the apparatus of FIG. 1 illustrating various controls.

Various fluid and control components of the system are illustrated in FIG. 5. Various components are shown schematically and may be suitably supported by the planar surface 14, support structure 16, or other suitable means. Such components include air over oil reservoirs 90, 92 connected to opposite ends of the rodless cylinder 42 through a flow control valve 94 having a lock valve 95 incorporated therewith, and through conduit 96. The oil reservoirs 90, 92 are coupled through conduits 98, 98 to opposite ends of an automatic, solenoid operated, directional control valve 100 which is coupled to the controller 18. Air is supplied from a suitable source to the valve 100 through a filter/regulator 99 and conduit 97.

The controller 18 includes a printer 110, a keyboard 112 having a start switch 14, a logic board 115, a display 116, and a power supply 117.

Prior to operation of the system, a hosiery article waistband or welt portion 111 is stretched slightly so as to be positioned over the end portions 21, 21 of fingers 20, 24 as shown by FIG. 1. The fingers at the home or start position are spaced with the opposed outer peripheries of portions 21, 21 having a predetermined distance therebetween, for example, six inches. The rotatable finger 20 attached to the load cell 22 permits any unequal tensions in the upper and lower parallel runs of the waistband 111 to equalize.

In operation, the controller 18 of the system is activated by actuating the start switch 114 on the keyboard 116. The controller, in turn, moves the valves 100, 95, 95 to the appropriate state to direct fluid to the rodless cylinder 42 to displace member 52, finger plate 38, shaft 36, bracket 34 and displaceable finger 24 to the left, FIG. 3 in a direction away from the finger 20. As the finger 24 moves, the controller monitors the force applied to the load cell 22 as the waistband 111 is stretched. When the force equals a predetermined, preprogrammed value, for example twenty-six pounds, the controller then records, via the encoder, the extended distance between the fingers 20, 24. This provides one of the parameters to be measured.

Throughout the specification and claims, the "distance" between fingers refers to the distance between the opposed, outermost peripheral surfaces of the fingers 20, 24.

When maximum stretch is determined and recorded by the controller, upon application of the predetermined, preprogrammed force to the waistband, the controller actuates the directional control valve 100 and through fluid reservoirs 90, 92 the rodless cylinder 42 starts moving the finger 24 back to the right, FIG. 3, towards the finger 20 to relax somewhat the waistband 111. The finger 24 stops at a preprogrammed, known, first stop position where compressive forces are measured and recorded. Upon movement of the finger to the first preprogrammed stop position, as determined by the timing belt 66 and encoder 60, the controller 18 energizes the lock valves 95, 95 to stop the rodless cylinder 42 having finger 24 coupled thereto. Once the finger 24 is at the first stop position, the controller 18 measures the compressive force applied by the waistband to the load cell 22 to determine whether the "fit" of a garment made from the hosiery article or articles will be acceptable.

After the measurement has been recorded, the controller 18 releases the lock valves 95, 95 and through reservoirs 90, 92, the rodless cylinder 42 retracts the finger 24 to its home position of FIG. 3, and the cycle has been completed.

Due to the aggregate delay of the operation of the system owing to variable components of the mechanism (latitude in various couplings, lag time in the operation of various valves, etc.), a calibrating stop for the finger 24 is necessary prior to taking the measurements at the first stop position. By first conducting such a calibrating stop, the accuracy of selected, preprogrammed distance between the two fingers 20, 24 is ensured.

A plurality of compression test stops may be programmed into the controller 18, as desired. As an example, compressive test stop measurements may be made with fingers spaced distances of fourteen, twelve, and ten inches from each other.

If the first compressive force test stop is to be made when the fingers are spaced apart twelve inches, for example, the calibrating stop must be conducted at some point prior to movement of the finger 24 to the first compressive stop position, for example, when the fingers are spaced apart thirteen inches. When the fingers are spaced thirteen inches as determined by the belt 66, encoder 60 and controller 18, the controller starts counting the pulses generated by the encoder between the thirteen inch distance, when the controller signaled the system to stop the finger 24, and the distance that the finger 24 continues to travel before it actually stops, which may be, for example, one-tenth of an inch. Since the lag time between the signal to stop the finger 24 and the actual stopping has been determined, on the first compressive test stop, the controller sends a stop signal when the fingers are twelve and one-tenth inches apart and the finger 24 stops with the fingers actually spaced twelve inches apart.

On subsequent compressive test stops, the one-tenth inch determined during the calibrating step prior to the first test stop is modified according to the result obtained on additional stops. Thus, the total number of stops during the testing of a waistband equals the total number of preprogrammed compressive stops plus one calibrating stop.

Figure 7:
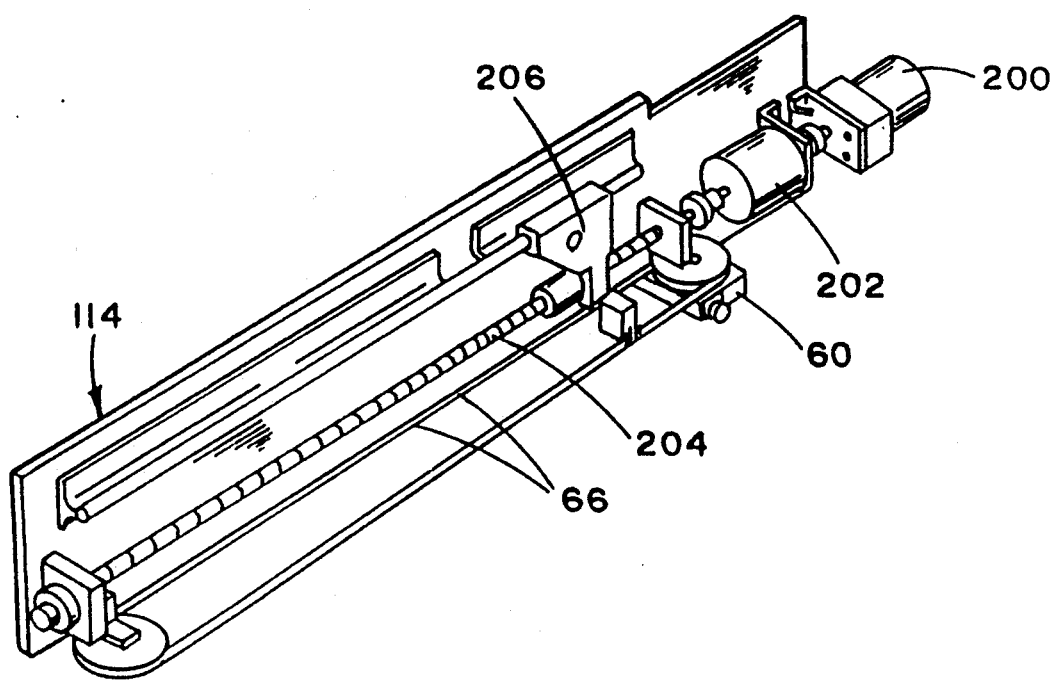
FIG. 7 is a modified embodiment of a mechanism for driving the movable finger.

The systems for driving the displaceable finger 24 could be of various types. As shown by FIG. 7, a reversible electric motor 200 may drive the finger 24 by means of a clutch 202, an elongated screw 204, and a finger supporting member 206 coupled to the screw.

In the drawings and specification, there has been set forth a preferred embodiment of the invention, and while specific terms may be employed, they are used in a generic and descriptive sense only and not for purposes of limitation, the scope of the invention being defined in the claims.

What is claimed as being new and what is desired to be protected by letters patent of the United States is as follows:

1. The method of automatically measuring elastic characteristics of a hosiery article waistband comprising the steps of: extending the article waistband over a fixed finger and a displaceable finger spaced apart a predetermined distance, applying a predetermined, preprogrammed force to the waistband to stretch the same by moving the displaceable finger relative to the fixed finger, measuring the distance between the fixed and displaceable fingers when the predetermined, preprogrammed force has been applied to the waistband, automatically retracting the displaceable finger towards the fixed finger to a preprogrammed first stop position located a predetermined distance from the fixed finger to partially relax the waistband, and automatically measuring the compressive force applied by the waistband to the fingers while the waistband is elongated to said predetermined distance determined by the first stop position, and further including the step of stopping the displaceable finger at a location prior to the finger reaching the first stop position to insure accuracy of the desired distance between the fingers at the first stop position.

2. The method of measuring elastic characteristics of a hosiery article waistband as claimed in claim 1, wherein the displaceable finger is sequentially retracted to a plurality of stop positions each located a predetermined distance from the fixed finger, and measuring the compressive force applied by the waistband to the fingers at each of the plurality of stop positions.

3. In a system for measuring the elastic characteristics of a hosiery article waistband to determine fit: a pair of spaced, relatively movable fingers adapted to receive thereover a waistband, means for displacing a first finger of said pair of fingers relative to a second finger of said pair of fingers, control means for regulating said displacement means to move said first finger away from said second finger to apply a predetermined force to said waistband and for actuating said displacing means to retract said first finger relative to said second finger to a first stop position with said first and second fingers spaced a predetermined distance, and means for measuring the compressive force applied by the waistband to said first and second fingers at said first position, each of said pair of fingers terminating in a portion having o-rings which engage inner portions of said waistband, and further including means rotatably mounting one finger of said pair of fingers to permit unequal tensions in the parallel runs of the waistband to equalize.

4. In a system as claimed in claim 3, said measuring means including means for determining the distance between said first and second fingers when said predetermined force is applied to said waistband.

5. In a system as claimed in claim 3, said control means including calibrating means for determining lag values in the system between the position of said first finger when a signal is issued by said control means to stop said first finger and the position of said first finger when said first finger actually stops.

6. In a system as claimed in claim 5 wherein said calibrating means includes an encoder actuated upon displacement of said first finger and means for determining the number of pulses generated by the encoder.

7. The method of measuring elastic characteristics of a hosiery article waistband to determine whether the waistband stretch is acceptable comprising the steps of: applying a predetermined force to the waistband to stretch the same by displacing a movable finger relative to a fixed finger, retracting the movable finger towards the fixed finger, initiating a signal to stop the movable finger, measuring the distance between the position of the movable finger when the signal was initiated and the stop position of the movable finger, again retracting the movable finger towards the fixed finger, stopping the movable finger at a predetermined position, initiating a signal when the movable finger is at a distance corresponding to said measured distance from the predetermined position, and determining the compression force of the waistband with the movable finger is at the predetermined position.

8. The method as claimed in claim 7 and further including the step of determining the maximum elongation of the waistband upon application of the predetermined force thereto.

* * * * *